(12) United States Patent
Froehlich

(10) Patent No.: US 11,282,034 B2
(45) Date of Patent: Mar. 22, 2022

(54) METHOD AND DEVICE FOR DELIVERING PATIENT SPECIFIC RADIOTHERAPY TREATMENT FROM A DERIVED TREATMENT PLAN

(71) Applicant: Brainlab AG, Munich (DE)

(72) Inventor: Stephen Froehlich, Aschheim (DE)

(73) Assignee: BRAINLAB AG, Munich (DE)

( * ) Notice: Subject to any disclaimer, the term of this patent is extended or adjusted under 35 U.S.C. 154(b) by 194 days.

(21) Appl. No.: 16/802,132

(22) Filed: Feb. 26, 2020

(65) Prior Publication Data

US 2020/0265538 A1    Aug. 20, 2020

Related U.S. Application Data

(63) Continuation of application No. 13/044,017, filed on Mar. 9, 2011, now abandoned.

(60) Provisional application No. 61/312,871, filed on Mar. 11, 2010.

(51) Int. Cl.
| | |
|---|---|
| *G06Q 10/10* | (2012.01) |
| *G16H 10/20* | (2018.01) |
| *G06F 40/186* | (2020.01) |
| *G16H 70/20* | (2018.01) |
| *G16H 80/00* | (2018.01) |

(52) U.S. Cl.
CPC .......... *G06Q 10/10* (2013.01); *G06F 40/186* (2020.01); *G16H 10/20* (2018.01); *G16H 70/20* (2018.01); *G16H 80/00* (2018.01)

(58) Field of Classification Search
CPC ........ G16H 10/60; G16H 40/67; G16H 50/70; G16H 50/50; G16H 20/40; G16H 70/60; G16H 10/40
See application file for complete search history.

(56) References Cited

U.S. PATENT DOCUMENTS

| | | |
|---|---|---|
| 2002/0082480 A1 | 6/2002 | Riff et al. |
| 2005/0159981 A1 | 7/2005 | Nagaeda et al. |
| 2005/0256745 A1 | 11/2005 | Dalton |

(Continued)

OTHER PUBLICATIONS

Pena J, González-Castaño DM, Gómez F, et al. eIMRT: a web platform for the verification and optimization of radiation treatment plans. J Appl Clin Med Phys. 2009;10(3):205-220. Published Jul. 21, 2009. doi: 10.1120/jacmp.v10i3.2998 (Year: 2009).*

*Primary Examiner* — Joseph D Burgess
(74) *Attorney, Agent, or Firm* — Middleton Reutlinger

(57) ABSTRACT

A method and device is described for delivering radiation therapy beam arrangement and beam settings to a radiotherapy device treating a patient with a tumor based medical condition. Patient specific treatment parameters data for the medical condition are developed and modified by the system. The treatment parameters data includes at least radiotherapy beam arrangement or photon beam energy for treatment of the particularized patient tumor location. Patient specific treatment parameters data are derived from a selected treatment plan and may include outlining of the patient's tumor in the medical images, the relevant modified patient specific treatment parameters data transferred to a computer controlling the radiotherapy device to control and apply radiotherapy treatment to the patient according to the modified treatment data.

12 Claims, 16 Drawing Sheets

(56) References Cited

U.S. PATENT DOCUMENTS

| | | | |
|---|---|---|---|
| 2007/0078306 A1* | 4/2007 | Allison | A61N 5/103 600/300 |
| 2008/0152085 A1 | 6/2008 | Saracen et al. | |
| 2008/0181362 A1 | 7/2008 | Gertner | |
| 2009/0125335 A1 | 5/2009 | Manetta et al. | |
| 2011/0106563 A1* | 5/2011 | Kresl | G16H 20/10 705/3 |
| 2012/0066000 A1 | 3/2012 | Opfer et al. | |

* cited by examiner

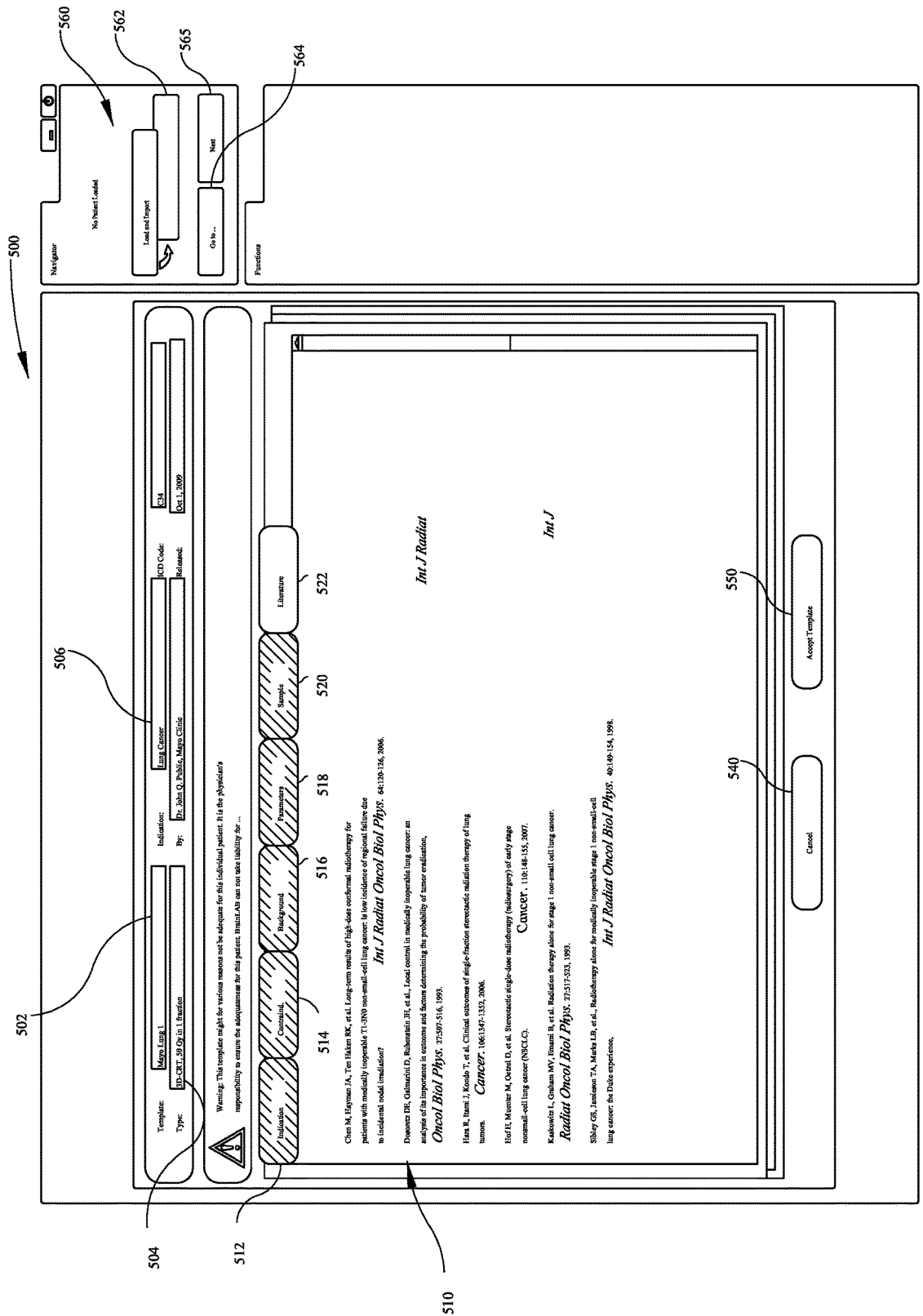

METHOD AND DEVICE FOR DELIVERING PATIENT SPECIFIC RADIOTHERAPY TREATMENT FROM A DERIVED TREATMENT PLAN

FIELD OF THE INVENTION

Aspects of the claimed invention relate to a method and device for delivering radiation therapy, including beam arrangement and beam settings, to a patient with a tumor based medical condition. Patient specific treatment parameters data for a tumor based medical condition are developed. The treatment parameters data from a selected treatment template file may include at least radiotherapy beam arrangement or photon beam energy for treatment of the tumor based medical condition. Patient specific treatment parameters data are then derived from the treatment template and are the modified according to patient specific data and may further include outlining of the patient's tumor in the medical images. The patient specific treatment parameters data is then transferred to a radiotherapy device to control and apply radiotherapy to the patient accordingly to the modified patient specific treatment parameters data.

SUMMARY OF THE INVENTION

The present invention provides a method and system for creating and distributing medical treatment protocol templates, which contain treatment parameters for treating a disease or medical condition. In one aspect of the invention, a method of providing a medical treatment protocol template, stored in electronic format to a user, includes receiving, at a computer system, a request for a treatment protocol template related to a medical condition of interest to a user; processing the request and identifying, from a database including a plurality of medical treatment protocol template files, at least one treatment protocol template related to the request; and transmitting the at least one medical treatment protocol template to the user.

The medical treatment protocol template may include treatment parameters data and optionally sample case data. The medical treatment protocol template may also include data chosen from indication data, a disclaimer, contra indication data, background information, one or more reference citations, or a combination of two or more thereof.

The database may be resident on a computer or server local to a user. The database may be resident on a server remote from a user's computer from which the request is made.

Transmitting the at least one medical treatment protocol template may include transmitting the at least one medical treatment protocol template to a user via a network connection, such as over the Internet, or may include transmitting an electronic copy of the at least one treatment protocol template to a user via e-mail.

The method may also include applying, such as known via a treatment planning application, the treatment parameters data of the at least one medical treatment protocol template to relevant patient data to create a patient specific treatment plan.

The method may include providing an online forum mode via the computer system for a user to interact with one or more clinicians regarding the at least one identified medical treatment protocol template.

A request from a user may include receiving a user response to one or more medical related questions; receiving one or more keywords as input; receiving a response to a user's selection of a medical condition from a list, or a combination of two or more thereof.

In another aspect of the invention, there is provided a system for providing a medical treatment protocol including a memory; a plurality of treatment protocol template files stored in the memory; and a processor that executes logic to receive a request for a medical treatment protocol template related to a medical condition, and identifies at least one treatment protocol template file related to the request, wherein a medical treatment protocol template file includes treatment protocol parameters data and sample case data.

The system may include a treatment planning application including patient files having patient data associated therewith for a respective patient, and the processor may execute logic to apply a relevant portion of the treatment parameters data associated with the at least one identified treatment protocol template to the appropriate patient data.

The processor may execute logic to transmit a copy of the at least one identified treatment protocol template to a user system requesting a treatment protocol template.

The system and method for distributing medical treatment protocol templates provides easy access to treatment protocols. The treatment protocol templates provide treatment protocol information in a readily accessible and usable form, which is often not available to clinicians and especially is often not readily available at the treatment planning system. The system and method allow a clinician to find a suitable treatment protocol without having to scour medical journals or publications (even online versions of such publications) and without having to read through an entire publication to find pertinent treatment protocol information, such as the actual treatment parameters, which may take a substantial amount of time.

Additionally, the treatment protocol templates provide, in one aspect of the invention, both treatment parameters data and sample case data. Sample case data may be beneficial to a clinician before applying a treatment protocol to their own patients. But such information is frequently not available in a publication's or journal's reporting of a treatment protocol.

Further, the method and system allow for the automatic transfer of the treatment parameters data, which relate to the treatment protocol itself, to patient data contained in, for example, a treatment planning application, to create a treatment plan specific to a patient that is to be treated using the treatment protocol. This may reduce the possibility of errors in manually entering the treatment parameters into a treatment planning system or manually entering the patient data in the appropriate treatment parameters field and may reduce the time to provide a patient-specific treatment plan.

In another aspect of the invention, there is provided a method for a medical treatment protocol system owner to create a medical treatment protocol template database including acquiring information regarding treatment of particular medical conditions including treatment parameters data and optionally sample case data related to the medical treatment protocol; converting the information into respective treatment protocol templates including the treatment parameters data, and optionally the sample case data associated with the treatment protocol; and saving the medical treatment protocol template as part of a database.

Acquiring information regarding treatment of a medical condition may include receiving a submission of data in electronic form from a clinician of the medical treatment protocol system owner. The submission of data from the clinician may be received in an e-mail format from a user or from the clinician uploading the data to the medical treatment protocol system.

In still another aspect of the invention, a method of treating a disease includes submitting a request for a medical treatment protocol related to a medical condition of interest to a medical treatment protocol system having a database including a plurality of medical treatment protocol templates; receiving an electronic version of at least one medical treatment protocol template from the treatment protocol system, the medical treatment protocol template including treatment parameters data and optionally sample case data; and treating a medical subject by performing treatment parameters defined in the at least one treatment protocol template on a medical subject.

The method of treating a patient may include applying relevant treatment parameters data of a medical treatment protocol template file to patient data to create a patient-specific treatment plan. A treatment planning application may be configured to interact with a treatment protocol template and apply at least a portion of the treatment parameters data to a patient treatment plan file including medical data related to a patient to create a patient-specific treatment plan.

These and other features of the present invention will become apparent from the following detailed description in conjunction with the drawings.

BRIEF DESCRIPTION OF THE DRAWINGS

In the annexed drawings:

FIGS. 11-16 illustrate an example of display outputs depicting exemplary aspects of medical treatment protocol template in accordance with aspects of the disclosed technology, wherein the display outputs pertain to a template different from that shown in FIGS. 5-10.

DETAILED DESCRIPTION

Aspects of the disclosed technology relate to a method and system for providing medical treatment protocols to clinicians for treating a medical condition. The medical treatment protocol may be in the form of a medical treatment protocol template that may provide a user with medical treatment protocol data and optionally sample case data useful to a user, such as a clinician, to suitably treat a patient. It will be appreciated that a medical treatment protocol application may be implemented as part of a software program resident on and/or readable by a computing device such as, for example, a personal computer (see, for example, FIG. 2). Alternatively, the medical treatment protocol application may be implemented as part of a web-accessible application that may be accessed by a user via the Internet (see, for example, FIG. 1).

The present invention is described herein in terms of several exemplary embodiments that should be taken to be illustrative of the invention and not limiting thereof.

Figure 1:
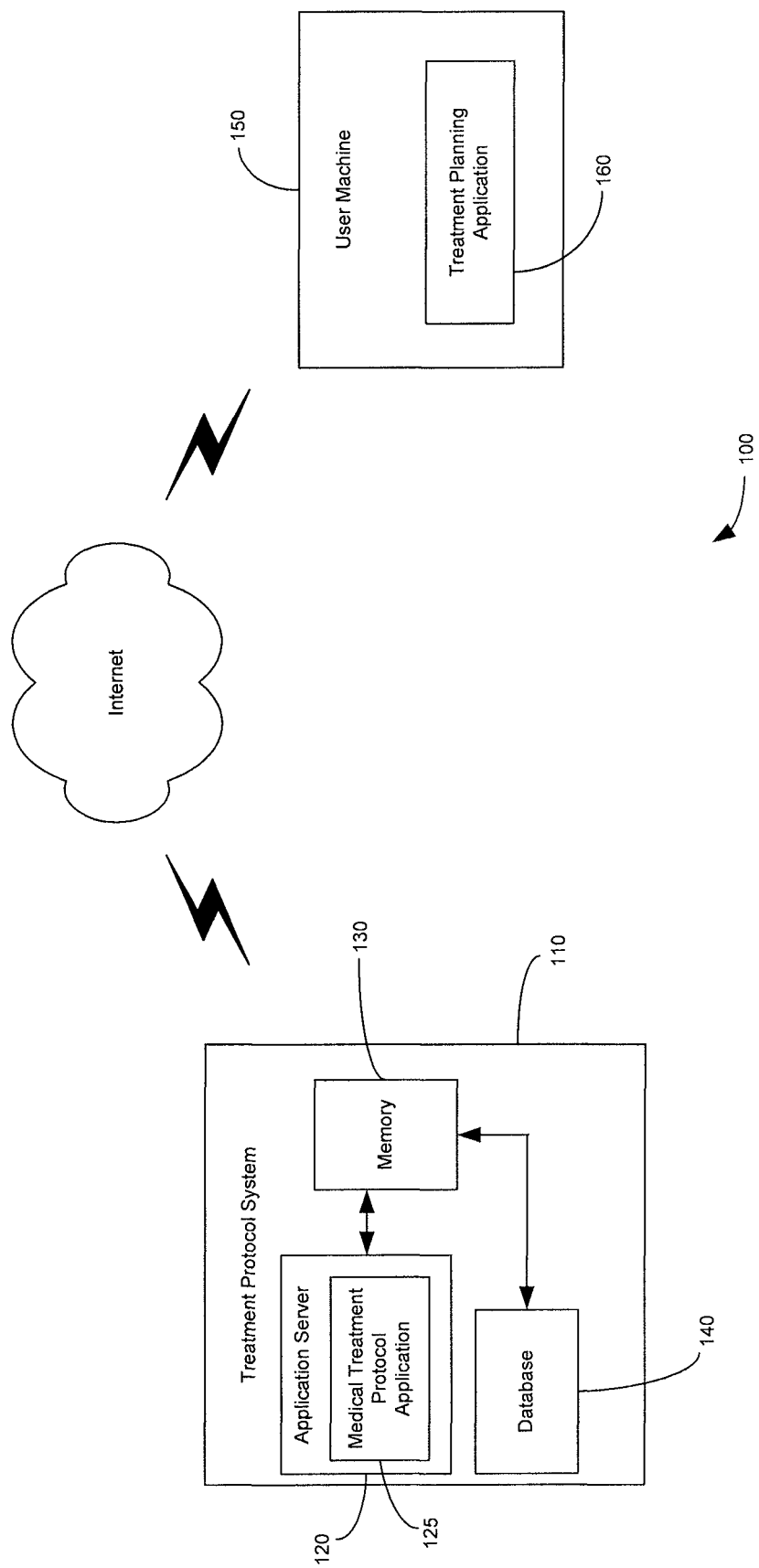
FIG. 1 is a functional block diagram of an exemplary web-based infrastructure on which aspects of the invention may be carried out.

Referring to FIG. 1, a medical treatment protocol application is illustrated in a general network or Internet environment 100 in which a medical treatment protocol system 110 includes an application server 120, a medical treatment protocol application 125, a memory 130 for storing data accessible or otherwise usable by the application server 120, and a database 140 which includes a plurality of medical treatment protocol templates. The medical treatment protocol templates may be in the form of electronic files, which may include textual, graphical, or audio content or a combination of two or more thereof. A user, such as a clinician, may access (using, for example, a machine 150) the medical treatment protocol template database 140 via the Internet to request and receive one or more medical treatment protocol templates. While shown as a separate element in FIG. 1, it will be appreciated that the database 140 may be incorporated as part of the memory 130.

Figure 2:
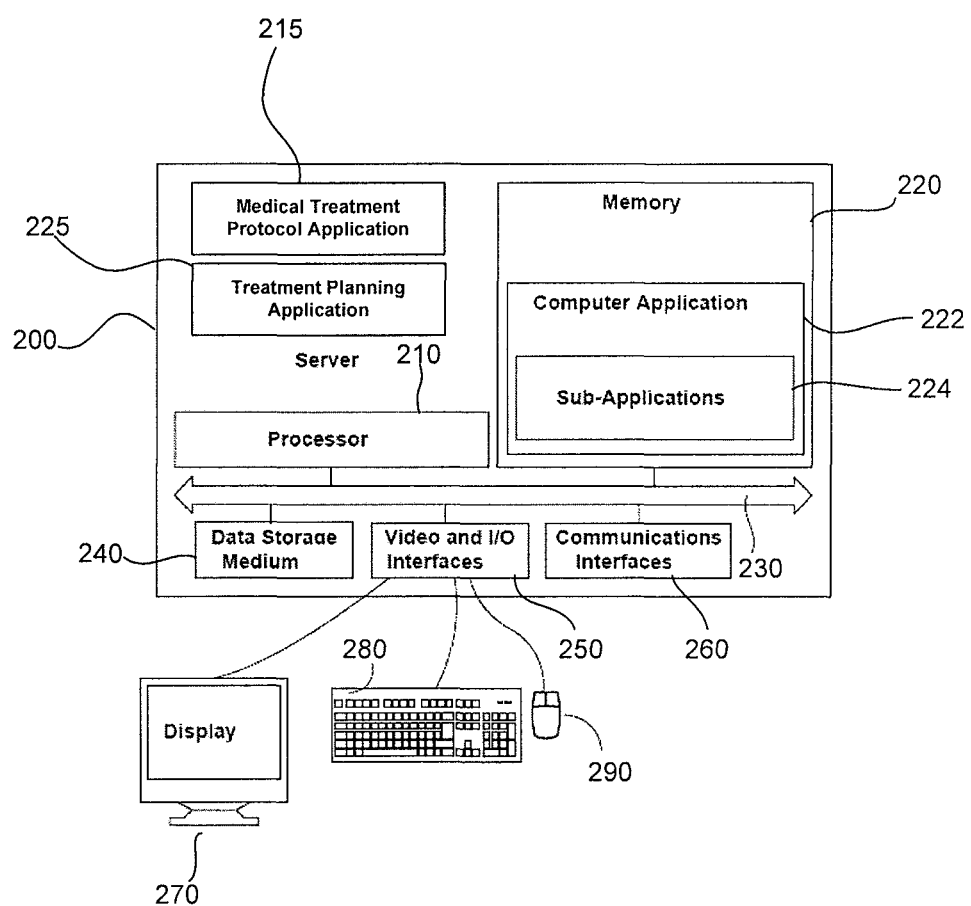
FIG. 2 is a functional block diagram of a computer or server as an exemplary machine on which aspects of the invention may be carried out.

Alternatively, the medical treatment protocol application and templates may be resident on a local computer or server. FIG. 2 illustrates a schematic block diagram of the server 200. The server 200 (also known as a data storage and web page hosting device) generally includes a processor 210, a memory 220, a local interface 230, a data storage medium 240, video and input/output interfaces 250, and various communication interfaces 260. The server may include optionally a display 270, a keyboard 280, and a user input device 290 (e.g., a computer mouse, a barcode scanner, a light pen, etc.). The server may be a personal computer or other suitable server capable of supporting a web-based application. The server is generally capable of executing one or more computer application(s) 222 in accordance with aspects of the present invention. The medical treatment protocol application 215 may include a database of medical treatment protocol templates. It will be appreciated that the medical treatment protocol database may be separate from, e.g., stored in the memory 220, but accessible by the medical treatment protocol application 215. In addition, the medical treatment protocol application may also include software (or computer-readable code) that permits information to be transmitted to and updated by various local and remote devices. The medical treatment protocol application may be logically associated with or call one or more additional computer applications 222 or one or more sub-computer applications 224, which generally include compilations of executable code.

In one embodiment, the medical treatment protocol application 215, the computer applications 222, the sub-applications 224, and/or treatment planning application 225 are embodied as one or more computer programs (e.g., one or more software applications including compilations of executable code). The computer program(s) can be stored on a data storage medium or other computer readable medium, such as a magnetic or optical storage device (e.g., hard disk, CD-ROM, DVD-ROM, memory stick, etc.).

To execute the computer application and associated database and sub-applications, the server or computer can include one or more processors 210 used to execute instructions that carry out a specified logic routine(s). In one embodiment, the server is based on a client-server architecture and may serve multiple clients. However, one of ordinary skill in the art will readily appreciate that any combination of computers having the functionality described herein shall be deemed to be within the scope of the present invention.

The server (e.g., 110 or 200) may have a memory for storing data, software, logic routine instructions, computer programs, files, operating system instructions, and the like. The memory can comprise several devices and includes, for example, volatile and non-volatile memory components. Accordingly, the memory can include, for example, random access memory (RAM), read only memory (ROM), hard disks, floppy disks, compact disks (e.g., CD ROM, DVD ROM, CD RW, etc.), tapes, and/or other memory components, plus associated drives and players for these memory types. The processor 210, memory 220, and the data storage medium 240 are coupled using a local interface 230. The local interface 230 can be, for example, a data bus with accompanying control bus, a network, or other subsystem.

The server can have various video and input/output interfaces 250 as well as one or more communications interfaces 260. The interfaces can be used to couple the server to various peripherals, such as a display (e.g., a CRT display, a LCD display, a plasma display, etc.), a keyboard, and a user input device. The communications interfaces 260 can include, for example, a modem, a network interface card, and/or a wireless network interface card. The communications interfaces 260 can enable the server to transmit and receive data signals, voice signals, video signals, and the like via an external network, such as the Internet, a wide area network (WAN), a local area network (LAN), direct data link, or similar wired (e.g., Ethernet) or wireless system (e.g., 802.11b or 802.11g). One of ordinary skill in the art will readily appreciate that a wireless communication medium and a wired communication medium may be used interchangeably to accomplish the functionality described herein and any such arrangement shall be deemed to be within the scope of the present invention.

In one embodiment, access to the medical treatment protocol application and/or database may be fee-based (e.g., monthly, quarterly, or yearly subscription) or non-fee based.

In one aspect, a medical treatment protocol template includes treatment parameters data and optionally sample case data related to a medical treatment protocol, and which is contained in a defined electronic format and structure. The format and structure, however, are not particularly limited and may be chosen as desired for an intended use or desired design.

Treatment parameters data may include parameters and conditions to be used during treatment of a particular medical condition. Each treatment parameter of a treatment protocol may be presented as a data field in a treatment protocol template. Examples of treatment parameters may include, but are not limited to, type of medication(s) to be used in treatment, dosage level(s) of medication to be used, number of treatments recommended, frequency of treatments, recommended time interval between treatments, treatment modality, criteria for patient selection for treatment (e.g., age, disease stage, tumor size, etc.), and the like.

It will be appreciated that other parameters may be included as desired depending on the specific medical condition and the treatment protocol. For example, in the field of radiation therapy and radiation, a treatment protocol may include parameters such as:

Dose to be given to the tumor
Maximum allowed dose for radiation-sensitive structures (i.e., organs at risk (OAR))
Number of treatment fractions
Beam arrangement
Treatment modality (e.g., intensity modulated radiation therapy (IMRT), Conformal Dynamic Arc, etc.)
Criteria for patient selection (e.g., age, disease stage, tumor size, etc.)

Sample case data may include data representing results from at least one example of the treatment protocol as applied to a medical subject. Such data may be presented and displayed in text form, table form, graphical form, audio, video or a combination of two or more thereof. Such data may be particularly beneficial to clinicians before applying a treatment protocol to a clinician's own patients. For example, such data may help clinicians who may not have experience with the protocol better understand the treatments, which will be beneficial in applying the protocol to their own patients.

Additionally, the medical treatment protocol template may include other data fields as desired. Such data may include, for example, data providing explanations related to the protocol and/or sample case data, different indications, contra indications, background information, citations to literature references discussing the treatment protocol, and the like. Such data may be presented and displayed in any suitable format including text or graphical representations. The treatment protocol template may also include a disclaimer field indicating, for example, that the protocol represented in the template may not be suitable for all patients or the particular patient for which the protocol was sought, and that it is the physician's or clinician's responsibility to ensure that the protocol is indeed suitable for the intended patient.

The medical treatment protocol application contains programming and logic to perform various functionalities suitable for use with aspects of the disclosed technology. The medical treatment protocol application may be configured to process a request for at least one medical treatment protocol template related to a medical condition or disease of interest to a user, identify at least one medical treatment protocol template from a database including a plurality of medical treatment protocol templates, and transmit the at least one identified template to a requesting device.

While in the context of the present example a request pertains to the particular medical condition of interest, the medical treatment protocol application can be configured to provide medical treatment protocol templates based on other criteria. For example, the medical treatment protocol application can be configured to provide a flat list of all available medical treatment protocol templates stored in the database (e.g., an unrestricted request). Similarly, the medical treatment protocol application can be configured to provide medical treatment protocol templates corresponding to a creator of the template, e.g., a particular clinician, a particular hospital, a particular university, etc. Such features can be advantageous, as different clinicians, hospitals, etc. may have different treatment philosophies that may result in different treatment parameters. By providing such search options, the clinician can be provided with different perspectives on how to treat a particular medical condition or disease.

In carrying out the various functions, the medical treatment protocol application may be configured to recognize various forms of input as a request for a medical treatment protocol template. For example, the medical treatment protocol application may be configured to recognize keywords or phrases received as input. The medical treatment protocol application may also be configured to provide a pre-programmed list of medical conditions and receive as input a user's selection of one or more of the listed medical conditions. As another example, the medical treatment protocol application may be programmed to provide a series of questions to be answered by a user to elicit information about a medical condition of interest. In providing questions to a user, the medical treatment protocol application may be configured to receive user-generated input (e.g., keywords or phrases) as a response to a question and/or may include pre-programmed choices (e.g., "yes" or "no" answers or pre-programmed phrases) from which the user may select in response to a question. Such questions could ask, for example, what the particular disease or condition is, what stage the disease is in, what is the patient's age, whether the patient is male or female, where a tumor is located, what size the tumor is, etc.

Figure 3:
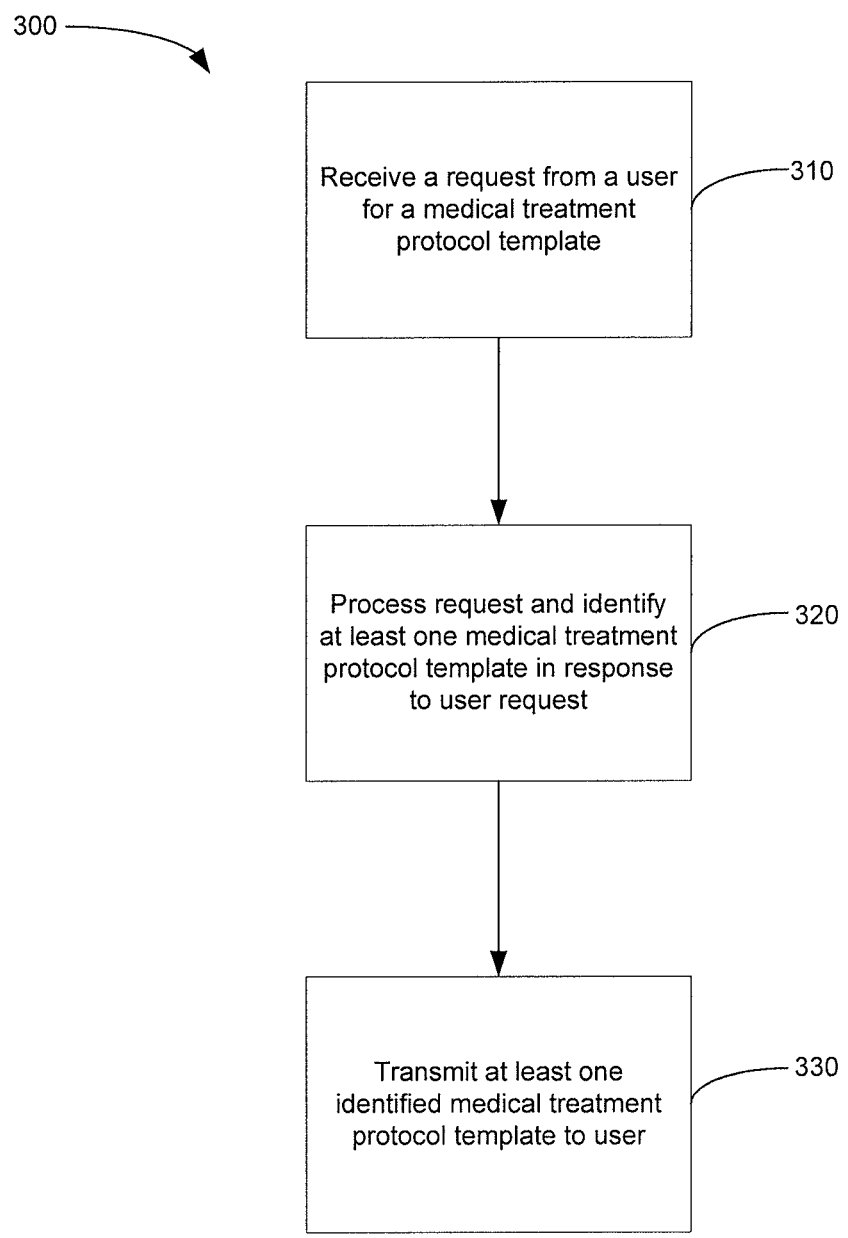
FIG. 3 is a flow chart illustrating an exemplary method of providing a medical treatment protocol template in accordance with aspects of the disclosed technology.

Referring to FIG. 3, a general method 300 for distributing a medical treatment protocol template is illustrated. At functional block 310, the method includes receiving, at a computer system, a request for a medical treatment protocol template related to a particular medical condition or disease. As described above, the method may be carried out in a web-based system. In such a system, as illustrated in FIG. 1, a user may operate the machine 150 to connect the system 110 and access the medical treatment protocol application 125 and request a treatment protocol template. Alternatively, referring to FIG. 2, a user's computer or server 200 may contain the database, and the request may be executed locally. Receiving a request may occur by, for example, the system 110 in FIG. 1 receiving an electronic request from a user machine 150. As another example, when the medical treatment protocol application is resident on a computer local to a user, such as, for example, server 200 in FIG. 2, the medical treatment application may receive the request by user input into the computer. As described above, the request may be in any suitable form including in the form of keyword input, user input in selecting a disease or condition of interest from a list or menu, or user input in responding to questions presented by the medical treatment protocol application, and the like.

At functional block 320, the medical treatment protocol application processes the request and identifies at least one treatment protocol template (e.g., a template stored on a database accessible by the treatment protocol application) related to the request. The number of treatment protocol templates identified may depend on the specificity of the request, the number of treatment protocol templates stored in the database, or a combination of such factors. It will be appreciated that the medical treatment protocol application may be programmed in any desirable manner to determine whether a treatment protocol template is identified as being responsive to the request.

At functional block 330, the medical treatment protocol application transmits the at least one identified medical treatment protocol template to the user. This step may include transmitting the medical treatment protocol template in a suitable electronic form for display by the end user. If more than one treatment protocol template is available and identified as a suitable match to a request, the medical treatment protocol application may transmit each identified treatment protocol template to the user and the output for display might be presented as a list from which the user may select one or more treatment protocol templates for review. If only one treatment protocol template is found, the output for display may be presented as a link, or the medical treatment protocol application may be programmed to automatically display the full version of the identified treatment protocol template upon being transmitted to the user. Further, the one or more medical treatment protocol templates may be transmitted as a complete template (i.e., a medical treatment protocol template containing all information associated therewith) or as a partial template (e.g., the medical treatment protocol template includes only information identifying a general description of the proposed treatment, only the treatment parameters, etc.). Transmitting and/or displaying only a general description of the proposed treatment is useful, for example, when a plurality of different medical treatment protocol templates are identified during a search, as it enables the clinician to quickly review the respective medical treatment protocol templates and exclude those that are not within the clinician's needs. Transmitting only the treatment parameters may be useful, for example, when the clinician already knows which medical treatment protocol template he intends to use, and only requires the specifics of the treatment.

Upon receiving the one or more treatment protocol templates, the clinician requesting the templates reviews the templates to determine if the treatment protocol defined in the template is suitable or acceptable for treating a respective patient. The clinician selects a particular template to use in treatment of a patient. If the clinician determines that the identified template(s) is/are not suitable for their use, they may choose to carry out another request.

In accordance with one embodiment, a patient-specific treatment plan may be created using the treatment protocol template(s) obtained from the request. Referring back to FIGS. 1 and 2, a user's computer (e.g., 150 or 200) may include a treatment planning application, e.g., treatment planning application 160 in FIG. 1 or treatment planning application 225 in FIG. 2. The treatment planning application may include patient treatment plan files containing patient data related to a respective patient. The patient data may include any desirable data including data such as the patient's height, weight, or age, the disease or condition to be treated, medical specific parameters such as disease stage, tumor size, or any other suitable parameter. The treatment planning application may be compatible with the medical treatment protocol application and/or medical treatment protocol templates to read, extract, and/or receive relevant data, e.g., treatment parameters data, contained in the medical treatment protocol templates that may be applied to the patient data in the patient treatment plan files.

In one embodiment, a user may be able to access potential treatment protocol templates through the treatment planning application. For example, a display associated with the treatment planning application, and in particular a patient treatment plan file, may include an icon or button that, when selected by a user such as by clicking on the icon, causes the treatment planning application to access a treatment protocol database to request one or more medical treatment protocol templates. Upon a clinician selecting a template as being suitable for treating a patient, the treatment parameters data may be automatically inserted into the treatment plan file that is being created or updated by the treatment planning application.

In the above embodiments, the request for the template may occur in any suitable manner as previously described herein. Additionally, depending on information contained in various parameters or fields of the patient treatment plan file, the medical treatment protocol application may pull up a subset of the database containing selected treatment protocol templates. For example, if the patient treatment plan file includes the name of a specific disease, e.g., prostate carcinoma, in a disease/condition field, the treatment protocol application may be configured to recognize such a field, or receive such information from the treatment plan file upon the user requesting access to the treatment protocol application database, and select templates related to the treatment of the specific condition.

Figure 4:
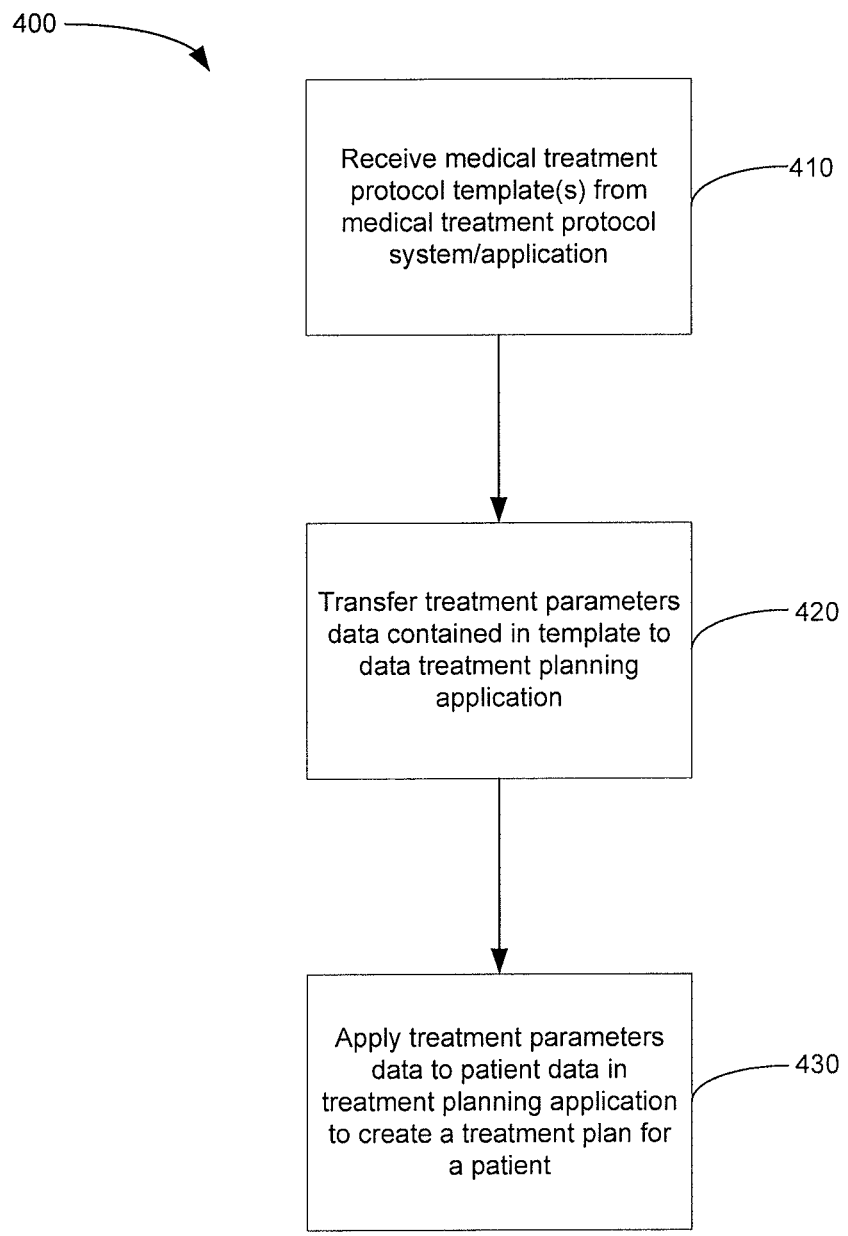
FIG. 4 is a flow chart illustrating a method of creating an exemplary patient-specific treatment plan from a medical treatment protocol template.

Referring to FIG. 4, a method 400 for transferring treatment data to a patient treatment plan is shown. At functional block 410, the user system (150 or 200) may receive a medical treatment protocol template from a medical treatment protocol system or application (if resident on a user's computer). At functional block 420, treatment parameters data are transferred to the treatment planning application. The treatment planning application may be configured to extract and/or receive treatment parameters data from a medical treatment protocol template and apply the parameters to patient data in a patient treatment plan file. Further, the treatment planning application may be configured to allow the clinician to modify the treatment plan, including treatment parameters. At functional block 430, the treatment planning application applies the treatment parameters data to a relevant patient data field in the treatment planning application and/or patient treatment plan file to create a patient-specific treatment plan employing an identified medical treatment protocol. By creating a patient-specific treatment plan from data associated with a treatment protocol template, the need for a user to manually enter information may be significantly reduced or eliminated. Automatically creating a patient-specific treatment plan may provide a time-saving benefit in that the treatment parameters need not be manually entered by a clinician, and may reduce or avoid the chance that incorrect information is entered in creating a treatment plan for a patient.

In providing treatment protocol templates, the treatment protocol system owner may also provide a manner in which a user may further communicate with the treatment protocol system owner to effectively implement the identified protocol in the treatment of a patient. For example, the treatment protocol system owner may provide various forums by which a user/customer can discuss various aspects of a treatment protocol with experienced clinicians and/or to provide suggested updates to the treatment protocols. The forum is not particularly limited and may include, for example, an online forum such as through an online chat or instant messaging system, live online web conferences including online video conferences, telephone conferences, and the like.

Another means by which the user may be supported in effectively implementing the identified medical treatment protocol template includes a case review. A case review may be thought of as a "second opinion", wherein one or more other clinicians provide their opinion of the treatment plan that the user created using the template.

As an additional service to the users of medical treatment protocol templates, fine tuning of the treatment plans created using the templates could be offered. Fine-tuning can go beyond the above "second opinion" in that the one or more other clinicians would not only provide advice, but would modify the created treatment plan as they deem appropriate.

In cases where a clinician or customer submits revisions or new treatment protocol templates to the system owner, a review process can be instituted wherein experts review the revisions or new templates. Once approved, the new or revised medical treatment protocol templates can be published and stored in the database. This may be particularly useful for medical treatment protocol templates submitted by clinicians/customers via email or online forums, as it provides a means to confirm that the submitted templates are in line with accepted medical practices. Further, if the medical treatment protocol template is published, the system owner may pay the creator of the medical treatment protocol template (e.g., a payment based on a fixed or sliding-scale), thereby providing an incentive to submit new medical treatment protocol templates.

FIGS. 5-10 illustrate an example of a display output 500 of a medical treatment protocol template in the form of a graphical representation suitable for display on a human-readable display. FIGS. 5-10 further illustrate how medical treatment protocol templates could be displayed within a treatment planning application (to which the navigation field 560 may belong; see below). As illustrated in FIGS. 5-10, the template may include a template name field 502, a treatment field 504, and an indication field 506. As illustrated in FIGS. 5-10, the indication field 506 indicates that the treatment protocol is related to the treatment of prostate carcinoma, and the treatment field 504 indicates that the protocol calls for a treatment modality of IMRT with 72 Gy in 40 fractions.

Figure 5:
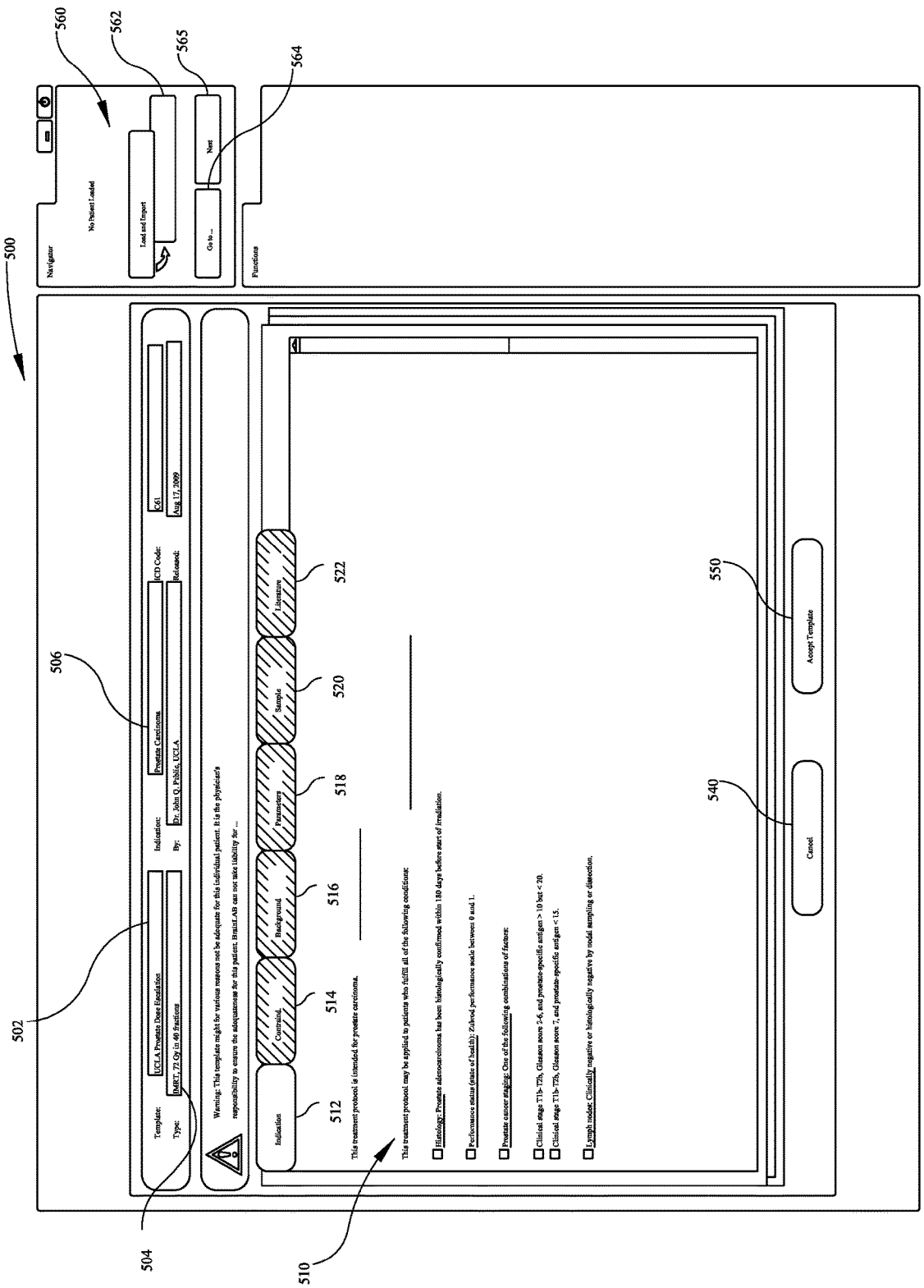
FIGS. 5-10 illustrate an example of display outputs depicting exemplary aspects of a medical treatment protocol template in accordance with aspects of the disclosed technology.
Figure 6:
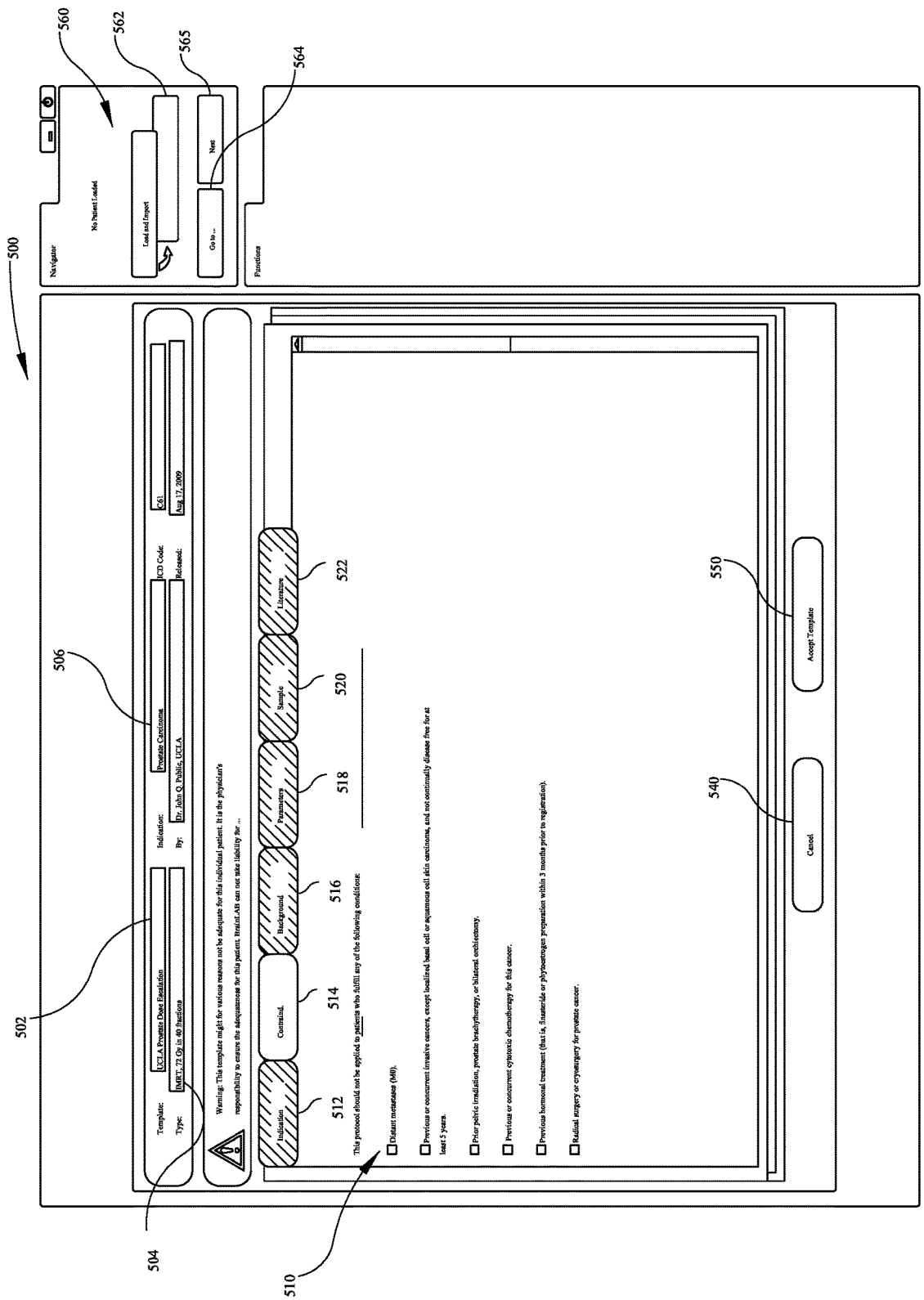
Figure 7:
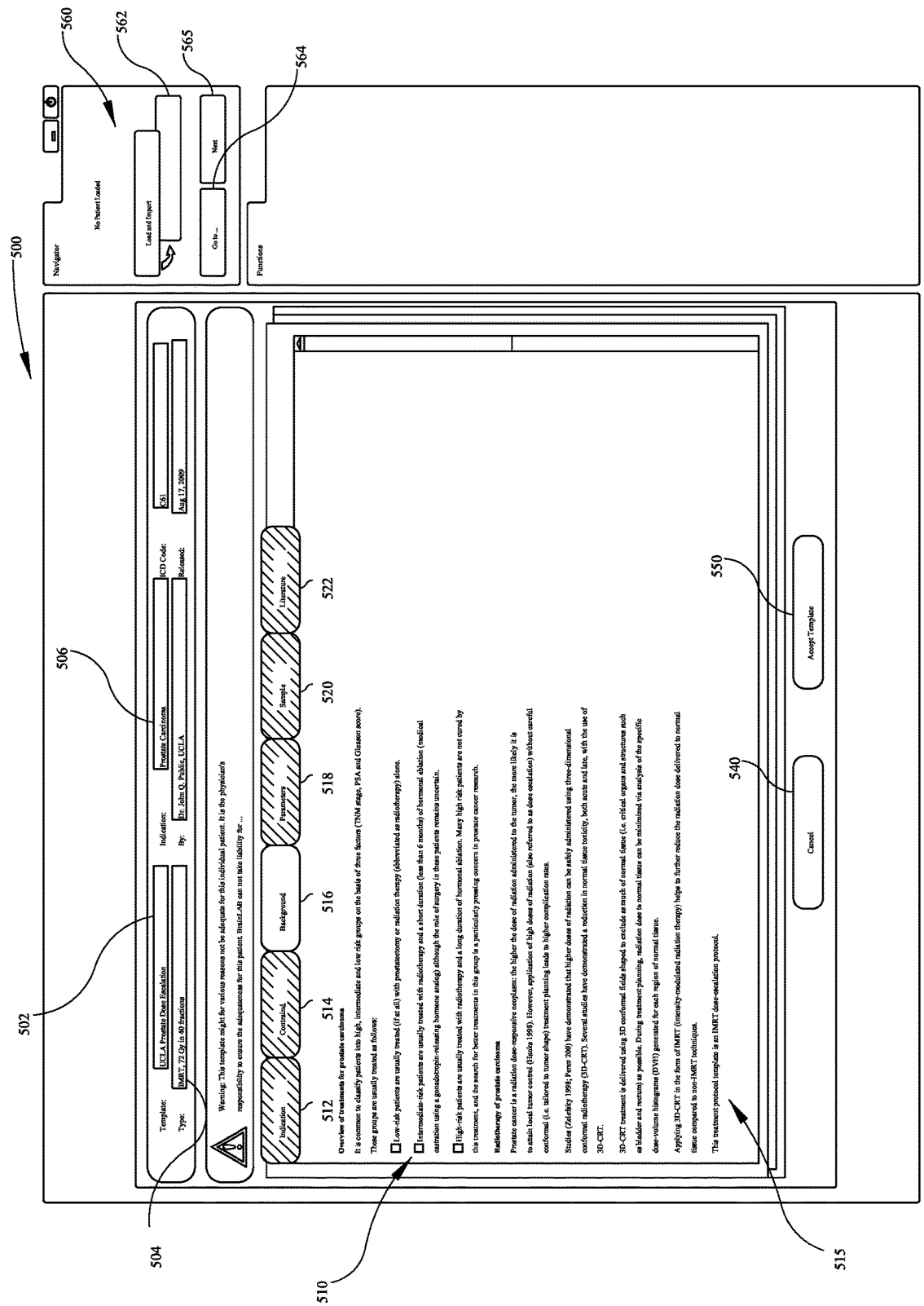

As shown in FIGS. 5-10, the display output includes a graphical section 510 containing various tabs with additional data fields. In FIG. 5, the display graphic associated with the indication icon 512 is shown to contain additional information related to the treatment such as the stage of prostate carcinoma for which the protocol is intended, how the treatment works, areas to be treated, and the like. FIG. 6 illustrates display output associated with a contra-indication icon 514, which provides information on disease and/or patient conditions that may make the particular protocol unsuitable for the user in a particular situation. FIG. 7 illustrates display output associated with a background icon 516. The display output shown in FIG. 7 is shown as including text output 515 providing information about the treatment and may also include video output (not shown) as a supplement to the text output 515.

Figure 8:
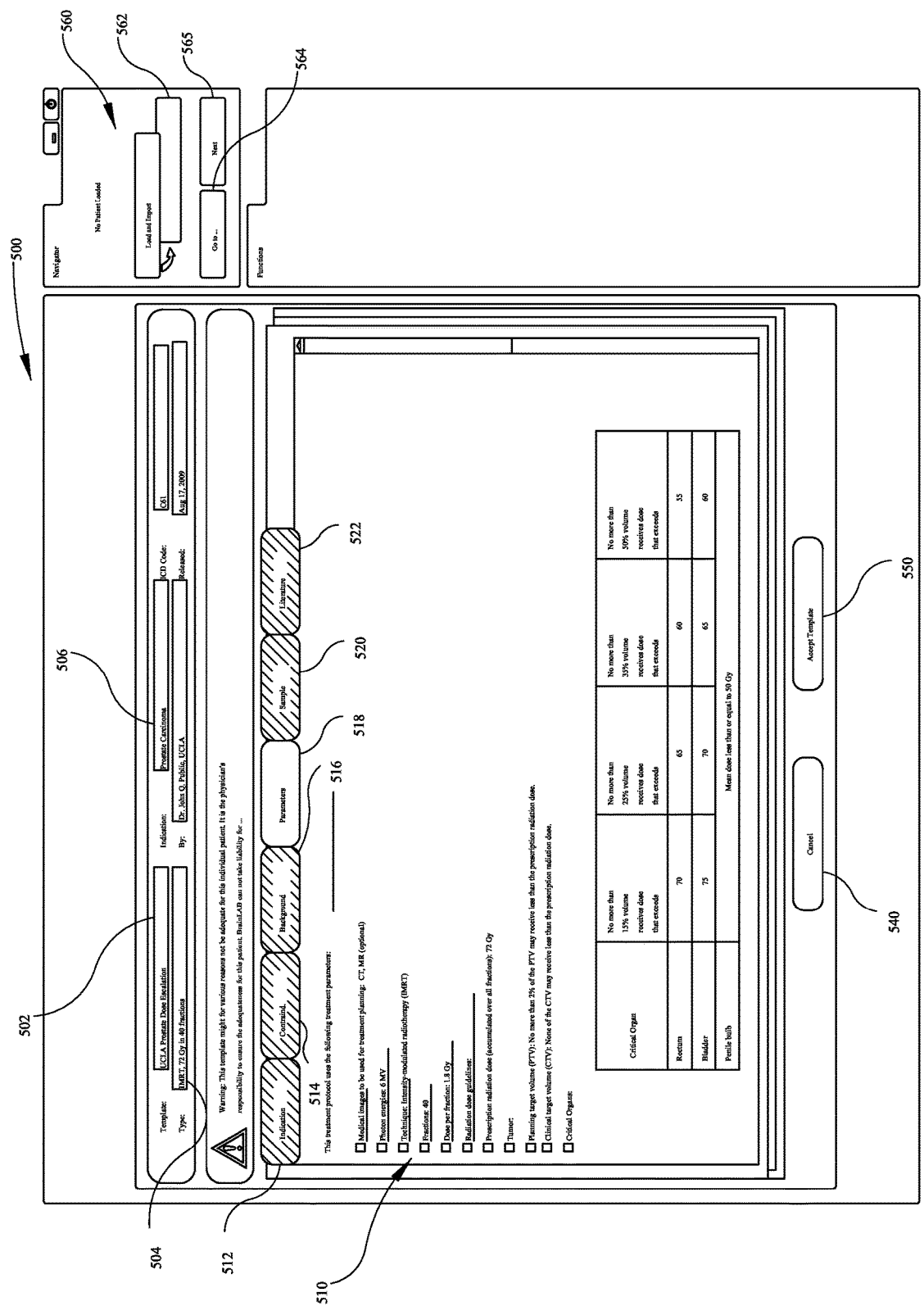

FIG. 8 illustrates data output associated with a parameter icon 518. As shown in FIG. 8, the data output illustrates the specific treatment parameters that may be used to treat the patient's medical condition or disease (Prostate Carcinoma in the present example). In the exemplary data output, the parameters include the medical images to be used or obtained, the photon energy setting of a particular piece of medical equipment, the application technique, the number of fractions, dose, etc. The data output may also include general guidelines on using the medical equipment, information regarding the target regions in or on the patient, critical organs, etc. As will be appreciated, the data output of the parameters screen in FIG. 8 can include any information that is relevant to treatment of the medical condition or disease.

Figure 9:
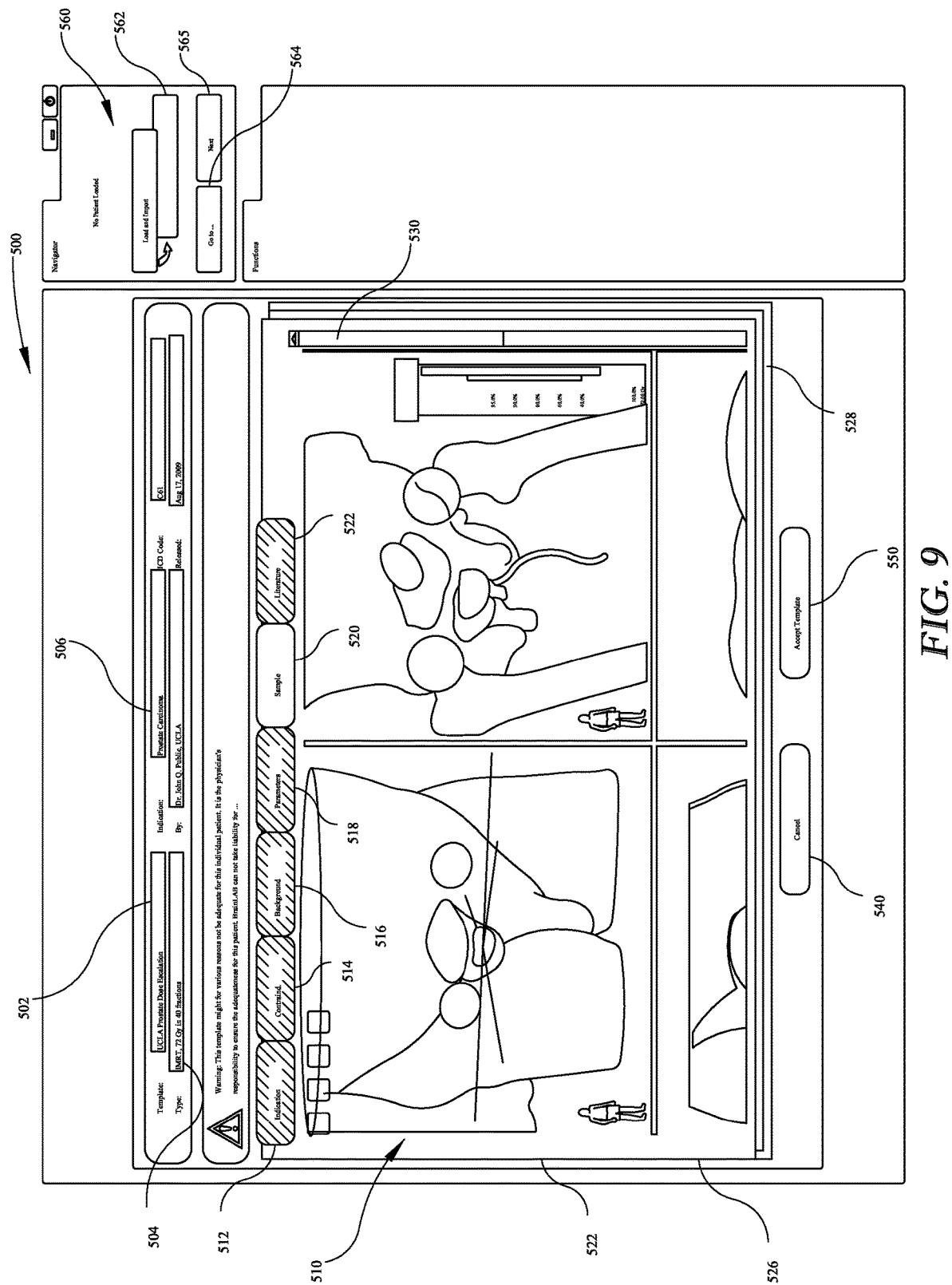

FIG. 9 illustrates data output associated with a sample case icon 520. In FIG. 9, the output is shown as a series of graphics 522, 526, or 528 (graphics 526 and 528 being more clearly visible if a user were to scroll down the display screen with scroll bar 530). Graphic 522 illustrates the arrangement of the IMRT beams used in a particular application. Graphic 524 illustrates a hotspot or area to avoid with the beams during treatment of this disease using the identified protocol.

Figure 10:
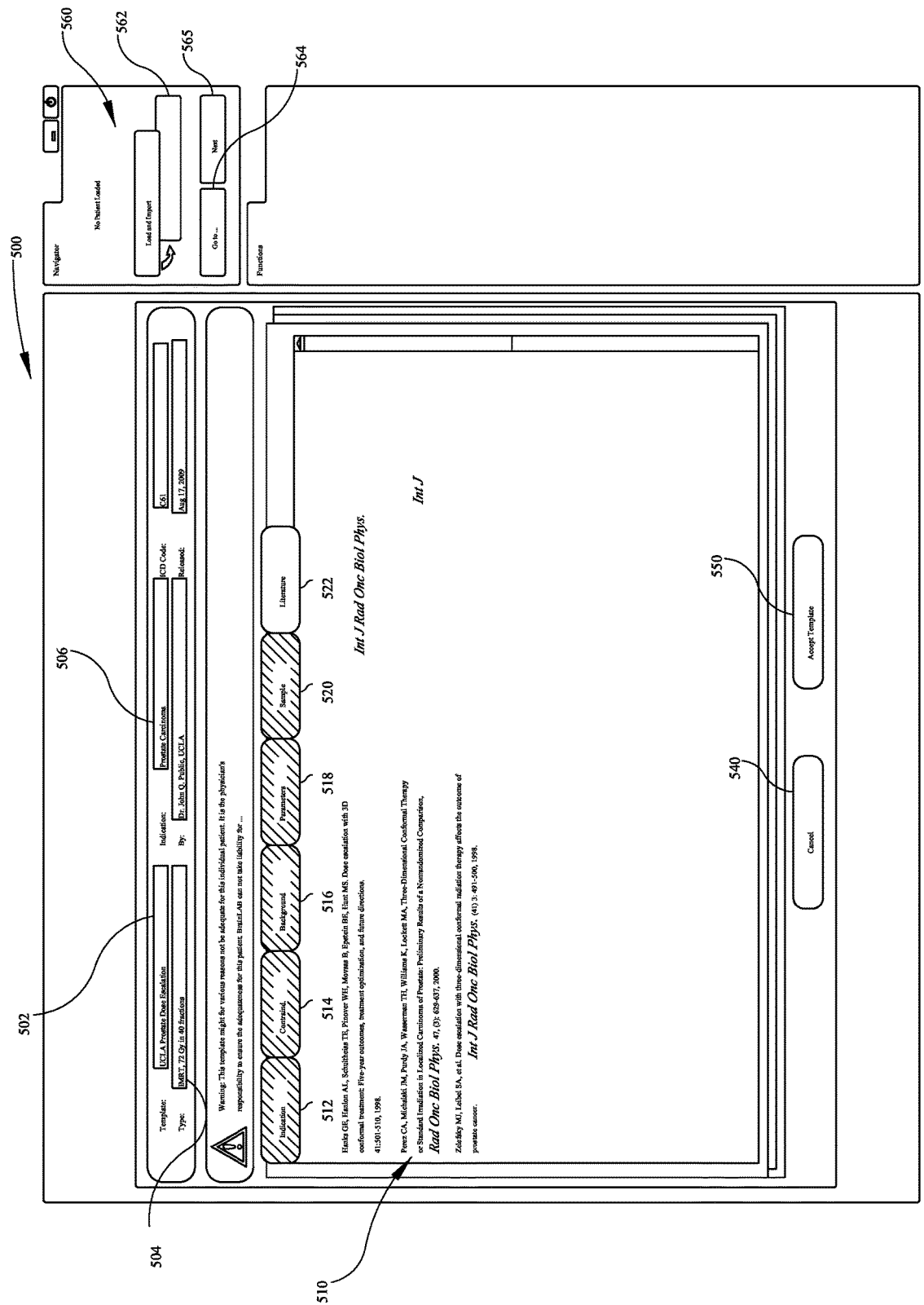
Figure 11:
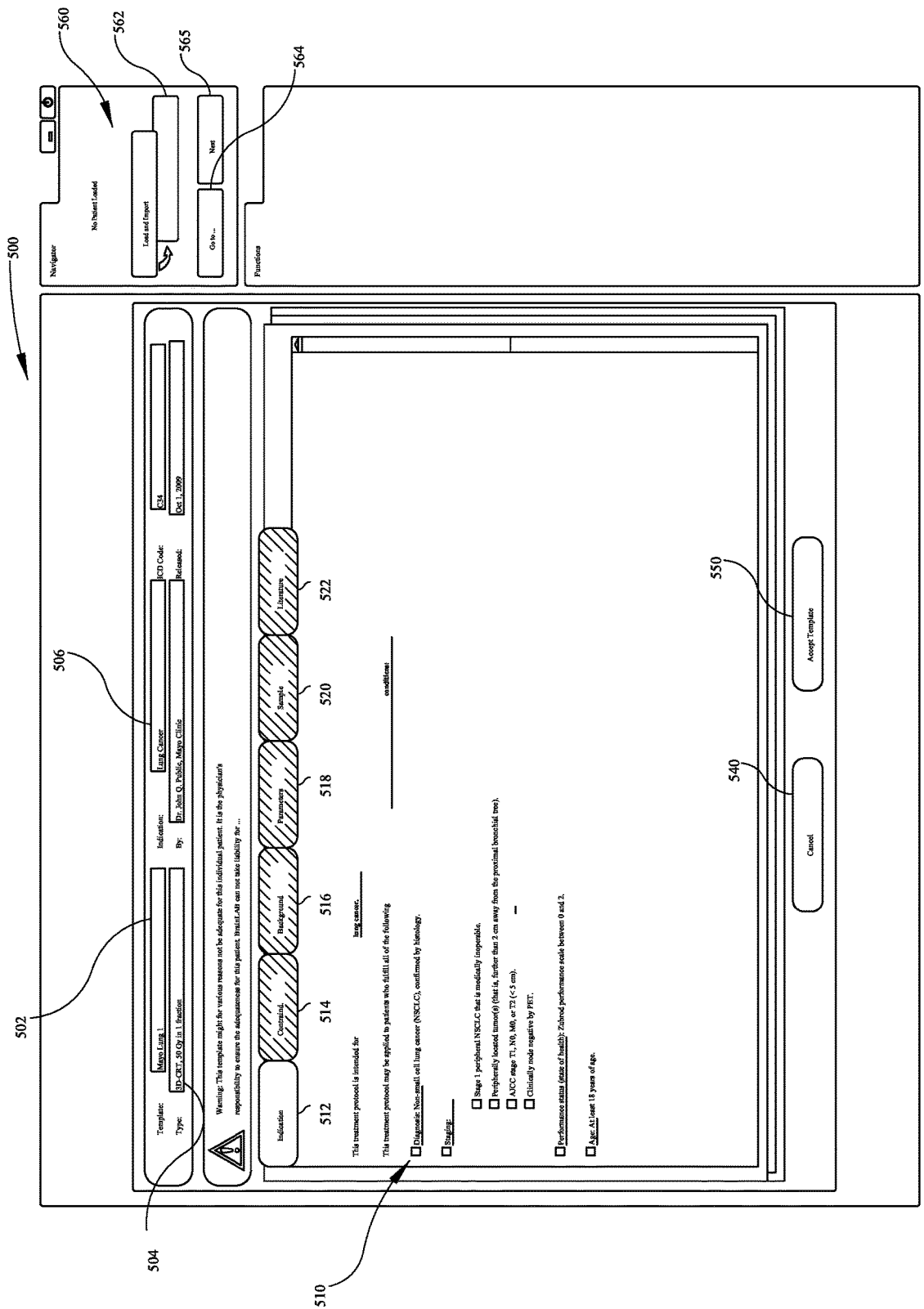
Figure 12:
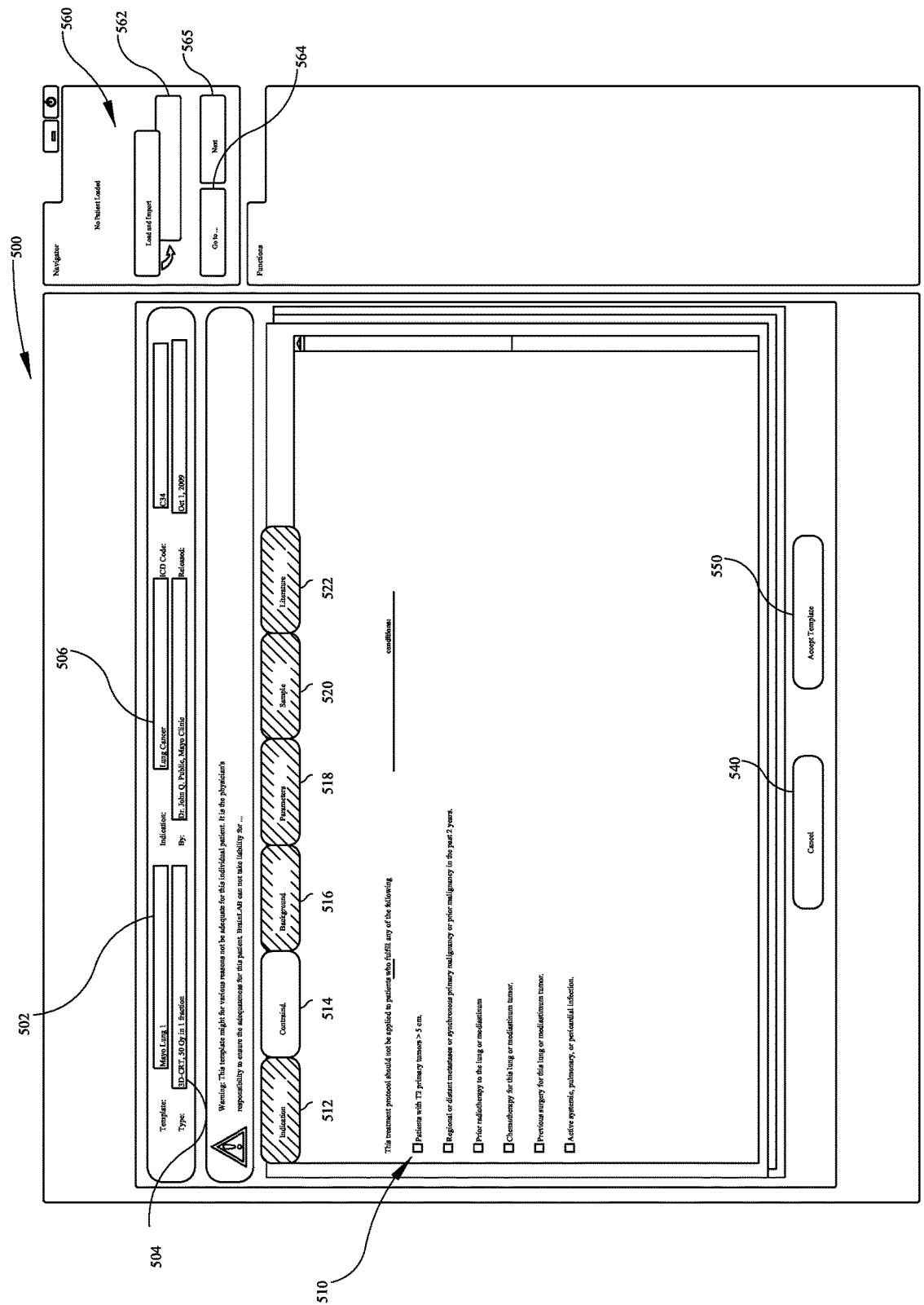
Figure 13:
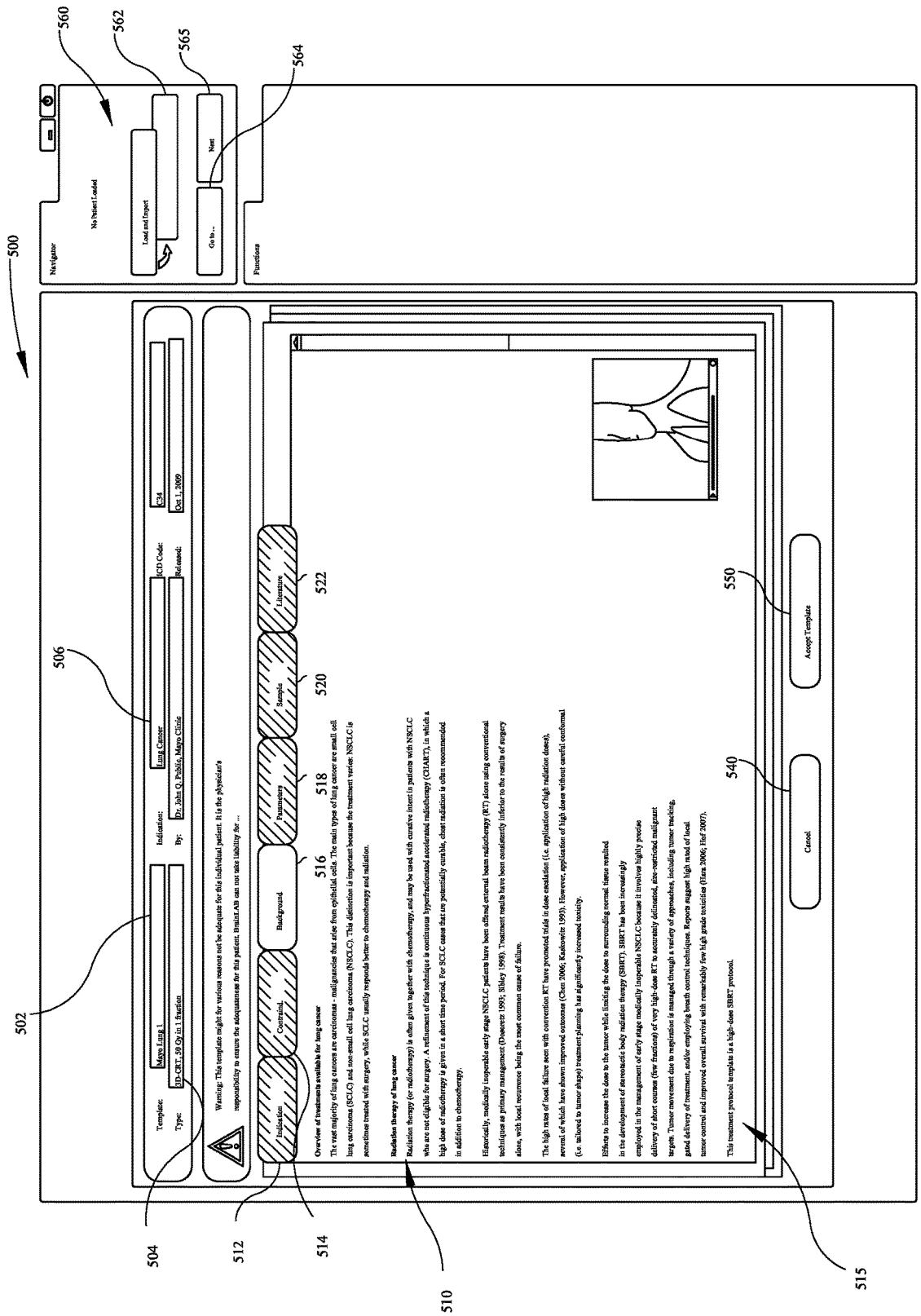
Figure 14:
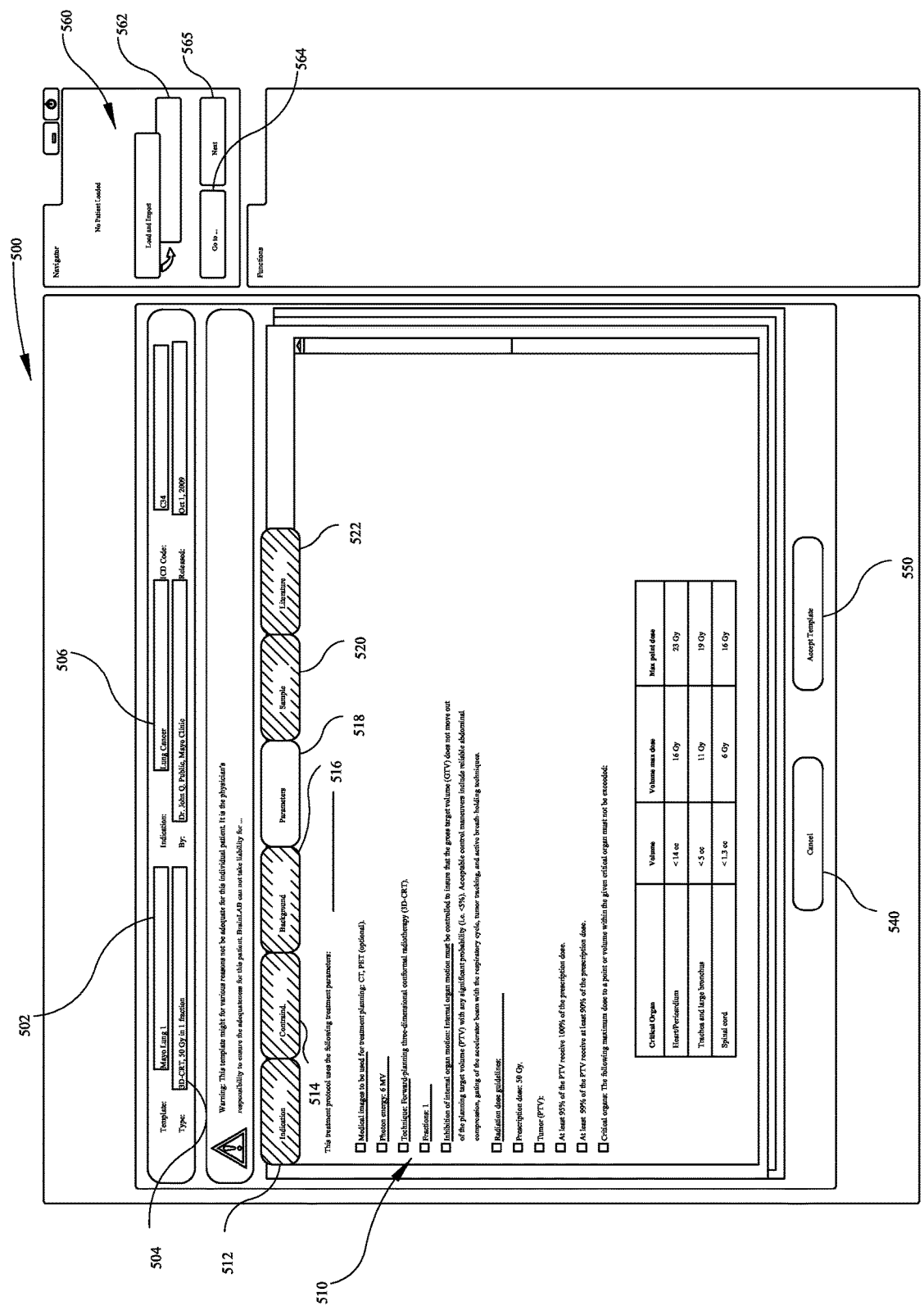
Figure 15:
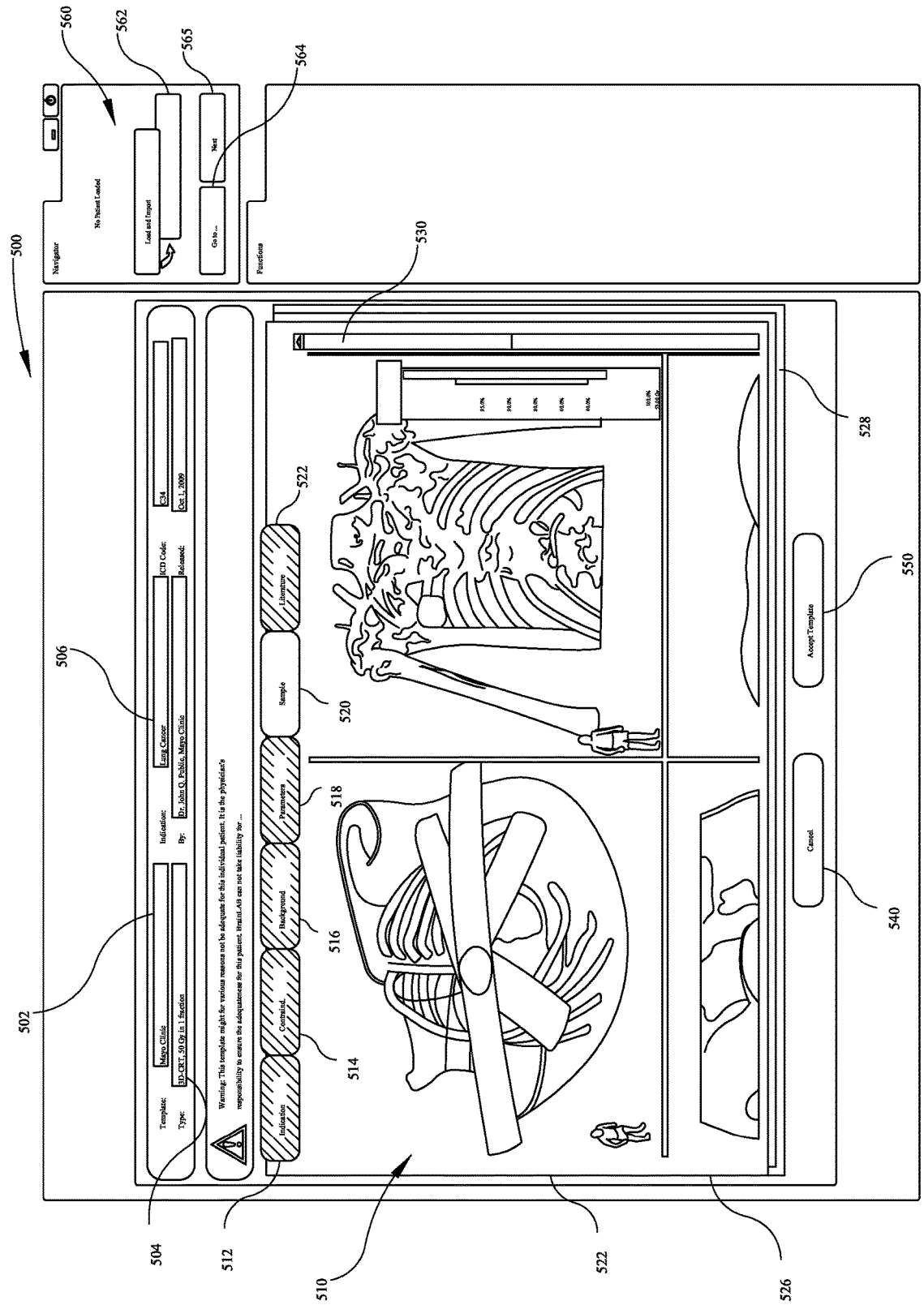

FIG. 10 illustrates a display of literature or reference data associated with the literature icon 522, which may include citations to various literature references or clinical studies discussing or applying the treatment protocol. It will be appreciated that the template may be configured to provide a link to the cited reference(s) that may be accessed via the Internet or a link to an electronic copy of the reference stored as part of the treatment protocol template.

In FIGS. 5-10, the output display of the medical treatment protocol template is also shown as including display fields 540, 550, and 560. Display fields 540 and 550 are illustrated as icons, which a user may click on or select to accept the template (field/icon 550), if they find the protocol acceptable for their needs, or they may click on cancel (field/icon 540) if the template is not suitable for their needs.

The display field 560 may be the navigation field of the treatment planning application. As previously described, the treatment parameters contained in the treatment protocol template may be transferred or imported to a patient treatment plan file to create a patient-specific treatment plan. In FIGS. 5-10, field 560 is shown as having no patient data, but provides field 562 to load a patient treatment plan file such as from a file stored on the treatment planning application. In one embodiment, by clicking the accept icon 550, the treatment parameters data may be automatically transferred to a patient treatment plan file loaded into the system.

The "Go to" and "Next" icons (564 and 565, respectively) of the treatment planning application may allow the user to jump to any (564) or just the next (565) step of the treatment planning workflow. Such steps may for example be the import of medical images, the outlining of anatomical objects (such as the tumor) in these images, or the selection and acceptance of an appropriate treatment protocol template (as described in the previous paragraph).

FIGS. 11-16 illustrate another exemplary display output 500 of a medical treatment protocol template. The format of FIGS. 11-16 is generally the same as that of FIGS. 5-10 and, therefore, will not be repeated. FIGS. 11-16 are provided to illustrate how the display output may appear for a different medical condition or disease (Lung Cancer in FIGS. 11-16).

A medical treatment protocol template may be created in any suitable manner. In one method, a medical treatment protocol system owner acquires information regarding treatment of particular medical conditions including treatment parameters data and optionally sample case data related to a medical treatment protocol, converts the information into the respective treatment protocol template, and saves the template as part of a database. Converting the acquired information into a template may include creating an electronic file having a defined format and structure to represent the information and provide it in a suitable format for a user. The template may be created to be compatible with other software, e.g., treatment planning software.

Generally, the medical treatment protocol data will be created by an individual or group of experienced clinicians. Such individual or group may be an existing customer of the medical treatment protocol system owner, engaged by the medical treatment protocol system owner to collect and/or create treatment protocol data, and/or a member of a group owned and/or operated by the medical treatment protocol system owner for providing medical treatment protocols. The individual or group of experienced clinicians may also include an institution such as a research center, hospital, or clinic that is an expert for the treatment of a specific disease. The group of experienced clinicians may also include an organization that plays a role in a certain medical field such as, for example, Novalis Circle, Radiation Therapy Oncology Group (RTOG), the American Association of Physicists in Medicine (AAPM), American Society for Therapeutic Radiology and Oncology (ASTRO), and the like.

The individual or group of clinicians may be engaged by the medical treatment protocol system owner to collect and/or develop data required for the medical treatment protocol templates. Alternatively, the individual or group of clinicians may pay a membership fee to the medical treatment protocol system owner for providing the service of centralizing, organizing, and providing the database of treatment protocols.

In acquiring the information related to treating the medical condition, the clinician or clinicians obtain information about a treatment protocol from one or more sources (e.g., publications, journals, etc.) The clinician(s) may filter or extract the relevant treatment protocol information from the source and submit it to the medical treatment protocol system owner.

In one example, a medical treatment protocol template and database may be created by receiving an electronic submission from, for example, a clinician or customer of the treatment protocol system owner. The submission may be provided in any suitable form. The submitter may submit the necessary data and information via e-mail or other suitable electronic form (e.g., PDF, word document, etc.). Alternatively, the treatment protocol system owner may provide an electronic form (e.g., via the treatment protocol system owner's website or software present on a computer local to the user) with various fields to be filled in by the submitter, and the electronic form may be submitted to the treatment protocol system owner.

The treatment protocol system owner may then have the submitted treatment protocol reviewed by a group of clinicians, e.g., a group that is a member of the treatment protocol system owner's organization or by a group that is engaged by the treatment protocol system owner to review such submissions. The clinician or group of clinicians reviewing the submitted treatment protocol data may approve of the submitted treatment protocol. If the treatment protocol submitted by the clinician or customer is approved, the treatment protocol system owner may use the approved protocol and data to create a treatment protocol template and add the template to its database. The treatment protocol system owner may require the party submitting the proposed protocol to agree to allow the treatment protocol system owner to modify the proposed protocol and to add any approved protocol and subsequently created template embodying the approved protocol to the treatment protocol system owner's database. As part of this model, the treatment protocol system owner may agree to compensate an individual or group whose submitted protocol and data is approved and incorporated into or created into a treatment protocol template.

In accordance with another aspect of the invention, there is provided a method of doing business in connection with the medical treatment protocol templates described herein. More specifically, a service provider may provide to one or more subscribers (e.g., hospitals, clinicians, etc.) access to application software and/or a database containing a plurality of medical treatment protocol templates as described herein. In exchange for the application software and/or access to the database, the subscriber pays to the service provider an agreed subscription fee. The subscription fee, for example, may be time-based, e.g., hourly, monthly, yearly, etc., or it may be use-based, e.g., a fixed fee each time the subscriber requests a medical treatment protocol template.

In providing access to the medical treatment protocol templates, the service provider may assemble, maintain, and update a database containing the medical treatment protocol templates. For example, the service provider may employ a staff of clinicians having expertise in various medical disciplines. The staff may modify, remove and/or develop medical treatment protocol templates as described herein, wherein the templates are stored in electronic format, e.g., on one or more computer servers operated by the service provider or provided to subscribers for use on the subscriber's computers via software update.

In addition to the above, clinicians and/or subscribers may submit new or revised medical treatment protocol templates to the service provider. In exchange for providing such medical treatment protocol templates, the clinician and/or subscriber may be provided with credits that can be used to pay for the subscription service.

To enable a subscriber to retrieve the medical treatment protocol templates, a user interface as described herein can be provided to easily search the database for medical treatment protocol templates. The user interface can include various search and sorting features as is conventional so as to enable efficient searching of the database. When the subscriber has found one or more medical treatment protocol templates that meets his/her needs, the one or more medical treatment protocol templates may be provided to the subscriber in any one of a number of different formats (e.g., emails, file download, physical media, etc.). In one embodiment, the medical treatment protocol templates are provided to the subscriber in encrypted form.

For systems configured with the medical treatment protocol templates and/or corresponding application software stored on the service provider's server, the user interface can include verification means to verify whether or not the subscriber has a valid subscription. This can be accomplished using conventional techniques, such requesting the subscriber to enter a characteristic identifier (e.g., enter a username and password via a web-based interface). Based on the characteristic identifier, the system can determine if the subscription is valid. If valid, then the subscriber is granted access to the system, and if invalid, then access is denied.

For systems configured with the medical treatment protocol database and corresponding application software stored on the subscriber's computer, the system may be configured to grant access for a specified time period corresponding to the subscription period. For example, if the subscriber purchased a one-month subscription, then the system will grant access (e.g., allow the application to run and/or grant access to the database) for a period of one-month beginning from the time the subscription was purchased. Once the time period has lapsed, then access to the application software and/or database may be denied until a new subscription is purchased.

As described herein, the application software and database need not reside on the same computer or server. It is possible, for example, for the application software to reside on the subscriber's computer, and the database to reside on the service provider's servers. It is also possible that the database resides on a third party's server (i.e., a party other than the service provider).

In another aspect, the disclosed technology provides a method and system for treating a medical condition. The method includes submitting a request for a medical treatment protocol related to treating a medical condition of interest to a medical treatment protocol system having a database including a plurality of medical treatment protocol templates. The party requesting the protocol then receives an electronic version of at least one medical treatment protocol template from the medical treatment protocol system relating to the medical condition of interest. As described above, this may be carried out as part of a web-based system or on a system local to the user. A medical subject may then be treated by performing treatment parameters defined in the at least one received treatment protocol template.

Upon receiving the medical treatment protocol template, a clinician may create a treatment plan for a medical subject by modifying and/or applying the treatment parameters data from the medical treatment protocol template to patient data of the medical subject. In one embodiment, as previously described herein, the clinician who will be treating the patient may have a treatment planning application containing the patient treatment plan file stored on a local computer and the treatment planning application may be configured to communicate with the medical treatment protocol template to automatically receive or extract the treatment parameters data from the medical treatment protocol template, apply the treatment parameters data to the appropriate patient data field in the patient treatment plan file, and create a patient-specific treatment plan with the treatment planning application. The data contained in the patient-specific treatment plan may be transferred to or read by a suitable program on a computer connected to a suitable piece of medical equipment for treating a patient. Further, prior to or after transfer, the treatment parameters and/or treatment plan may be manually modified by a medical professional as desired.

A person having ordinary skill in the art of computer programming, and specifically in interactive software programming should consider it obvious in view of the provided description how to program a device to operate and carry out the functions of the medical treatment protocol application, medical treatment protocol template, and/or treatment planning application described herein. Also, while the functionality of these applications may be carried out via a controller and/or a web access interface (alone or in conjunction with other application programs) in accordance with inventive aspects, such functionality also could be carried out via dedicated hardware, firmware, software, or combinations thereof without departing from the scope of the present invention.

Although the invention has been shown and described with respect to one or more particular preferred embodiments, it is clear that equivalent amendments or modifications may occur to the person skilled in the art when reading and interpreting the text and enclosed drawings of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment or embodiments illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

The invention claimed is:

1. A computer implemented method for controlling and delivering patient specific treatment of radiation therapy, comprising:
   connecting by electronic communication a computer system and a radiotherapy medical treatment device;
   creating, for an identified patient having a tumor based medical condition, a patient specific treatment plan containing patient specific treatment parameters data by at least one processor of the computer system;

controlling the radiotherapy medical treatment device with the patient specific treatment parameters data, the patient specific treatment parameters data including radiation therapy data including at least:
  a beam arrangement for the radiotherapy medical treatment device for treatment of a tumor of the identified patient;
  a photon beam energy setting for the radiotherapy medical treatment device for treatment of the tumor of the identified patient;
wherein creating the patient specific treatment plan containing the patient specific treatment parameters data for the identified patient includes at least:
  receiving, at the at least one processor of the computer system, a request for a treatment template related to the tumor based medical condition of the identified patient;
  identifying, by the at least one processor of the computer system, from an electronic database having a plurality of treatment template files, at least one treatment template related to the request, the at least one treatment template including treatment parameters data describing parameters and conditions to be used during treatment of the tumor based medical condition of the identified patient and criteria for patient selection for the treatment of the tumor based medical condition;
  wherein the treatment template includes at least sample case data, the sample case data including data representing results from at least one example of the treatment template as applied to a medical subject which is not the identified patient;
  transmitting by the at least one processor of the computer system, the at least one treatment template to an associated user including transmitting the sample case data and criteria for patient selection for the treatment of the tumor based medical condition of the identified patient for evaluation by the associated user;
  preparing for evaluation by the associated user, the at least one treatment template including the sample case data and criteria for patient selection for the treatment template of the tumor based medical condition of the identified patient for evaluation by the associated user;
  receiving, by the at least one processor of the computer system, patient-specific data, the patient-specific data describing the tumor based medical condition of the identified patient prior to treatment of the tumor based medical condition of the identified patient based on the treatment template, the patient-specific data comprising at least one medical specific parameter, the medical specific parameter being one of a disease stage and a tumor size for the identified patient for the tumor based medical condition;
  creating, by the at least one processor of the computer system, the patient specific treatment plan including the patient specific treatment parameters data and patient specific treatment conditions being created based on both the treatment template and the patient-specific data;
  modifying, using the at least one processor of the computer system, the created patient specific treatment plan, including the patient specific treatment parameters data;
  wherein the modified patient specific treatment parameters data includes the photon beam energy setting, patient areas to avoid with the beam and the beam arrangement for the identified patient and for the tumor based medical condition of the identified patient;
  transmitting by the at least one processor of the computer system, the patient specific treatment parameters data of the patient specific treatment plan for treating the identified patient to the radiotherapy medical treatment device; and
  controlling the radiotherapy medical treatment device with the patient specific treatment parameters data for the identified patient and for the tumor based medical condition of the patient specific treatment parameters data of the patient specific treatment plan for treating the identified patient with the radiotherapy medical treatment device based on the patient specific treatment parameters data including at least:
    the photon beam energy setting;
    radiation dose to be given to the tumor of the patient;
    areas to avoid with the beam; and
    the beam arrangement
  such that the radiotherapy medical treatment device operates under the modified patient specific treatment parameters data.

2. The method of claim 1, wherein the treatment template comprises data chosen from indication data, a disclaimer, contra indication data, background information, one or more reference citations, or a combination of two or more thereof.

3. The method of claim 1, wherein the electronic database comprising the plurality of treatment template files is resident on a user's computer.

4. The method of claim 1, wherein the electronic database comprising the plurality of treatment template files is resident on the computer system remote from a user's computer.

5. The method of claim 4, wherein transmitting the at least one treatment template includes transmitting the at least one treatment template to a user via a network connection.

6. The method of claim 1, further comprising manually modifying the patient specific treatment parameters data.

7. The method of claim 1, wherein the request for a treatment protocol template is made via a treatment planning application.

8. The method of claim 1 wherein the receiving the request for the treatment template related to the tumor based medical condition of the identified patient is received by a treatment protocol system running a treatment protocol application on the at least one processor.

9. The method of claim 8 wherein the transmitting by the at least one processor of the computer system the patient specific treatment parameters data of the patient specific treatment plan for treating the identified patient to the radiotherapy medical treatment device is transmitted by a user machine running a medical treatment planning application.

10. The method of claim 1 wherein the creating, by the at least one processor of the computer system, the patient specific treatment plan includes applying treatment parameters data in the treatment template to the patient specific treatment parameters data of the patient specific treatment plan.

11. The method of claim 10 wherein the creating of the patient specific treatment plan and the modifying of the patient specific treatment plan is done automatically by the at least one processor thereby avoiding incorrect information entered in the patient specific treatment plan.

12. The method of claim 1 wherein the patient specific treatment parameters data are derived from the identified treatment template and may further include modifying medical images of the tumor by outlining of the patient's tumor in the medical images.

\* \* \* \* \*